US008865069B2

(12) United States Patent
Gut et al.

(10) Patent No.: US 8,865,069 B2
(45) Date of Patent: Oct. 21, 2014

(54) APPARATUS AND PROCESS FOR OPENING AND CLOSING FLUID CONTAINERS (75) Inventors: Raphael Gut, Lucerne (CH); Gottlieb Schacher, Kriens (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 89 days.

(21) Appl. No.: 13/460,867

(22) Filed: May 1, 2012

(65) Prior Publication Data
US 2012/0301357 A1 Nov. 29, 2012

(30) Foreign Application Priority Data
May 25, 2011 (EP) .................................... 11167523

(51) Int. Cl.
B67B 7/00 (2006.01)
B67B 7/16 (2006.01)
G01N 35/00 (2006.01)
B01L 3/00 (2006.01)
G01N 35/04 (2006.01)

(52) U.S. Cl.
CPC ........ *B01L 3/50825* (2013.01); *G01N 35/0099* (2013.01); *B67B 7/00* (2013.01); *G01N 2035/0405* (2013.01); *B01L 2300/046* (2013.01); *B01L 2300/042* (2013.01)
USPC .................. 422/63; 422/65; 422/66; 422/67; 53/285; 53/476

(58) Field of Classification Search
CPC ............ B01L 3/50825; B01L 2300/04; B01L 2300/042; B01L 2300/046; G01N 2035/0405; B67B 7/00
USPC .............. 422/63–68.1, 500–501; 53/287, 476
See application file for complete search history.

(56) References Cited

U.S. PATENT DOCUMENTS

| 4,455,280 | A | * | 6/1984 | Shinohara et al. ............... 422/63 |
| 5,271,897 | A | * | 12/1993 | Wurschum et al. ............. 422/63 |
| 5,525,298 | A | * | 6/1996 | Anami ............................. 422/63 |
| 5,628,962 | A | * | 5/1997 | Kanbara et al. ................. 422/63 |
| 6,190,617 | B1 | * | 2/2001 | Clark et al. .................... 422/562 |
| 6,827,904 | B2 | * | 12/2004 | Kitagawa ....................... 422/509 |
| 6,866,820 | B1 | * | 3/2005 | Otto et al. ........................ 422/63 |
| 8,361,387 | B2 | * | 1/2013 | Schacher et al. ................ 422/63 |
| 8,501,094 | B2 | * | 8/2013 | Mototsu et al. .............. 422/68.1 |
| 2001/0028863 | A1 | * | 10/2001 | Kitagawa ....................... 422/100 |
| 2006/0088443 | A1 | * | 4/2006 | Mattila et al. ................... 422/63 |
| 2007/0110624 | A1 | | 5/2007 | Lare et al. |
| 2010/0080732 | A1 | * | 4/2010 | Mototsu et al. ................. 422/63 |
| 2012/0328475 | A1 | * | 12/2012 | Sakairi et al. ................... 422/67 |

FOREIGN PATENT DOCUMENTS

EP 0703457 B1 3/1996
EP 2287621 A1 2/2011

* cited by examiner

*Primary Examiner* — Brian R Gordon
(74) *Attorney, Agent, or Firm* — Roche Diagnostics Operations, Inc.

(57) ABSTRACT

An apparatus for the automated opening/closing of one or more fluid containers is presented. Each container comprises an opening and a cap for closing the opening. The cap is pivotable with respect to the container body so as to open or close the container. A mount and a carriage supported by the mount by a translating mechanism bidirectionally translate the carriage with respect to the mount. The carriage comprises a base portion and a pivoting portion supported by the base portion by a pivoting mechanism that bidirectionally pivots the pivoting portion with respect to the base portion. The pivoting portion has a contact member that contacts a projecting portion of the cap of each of the fluid containers while pivoting the pivoting portion so as to open and optionally close the opening. A drive is coupled to the carriage for translating the base portion and pivoting the pivoting portion.

13 Claims, 8 Drawing Sheets

APPARATUS AND PROCESS FOR OPENING AND CLOSING FLUID CONTAINERS

CROSS-REFERENCE TO RELATED APPLICATIONS

This application is a continuation of EP 11167523.7, filed May 25, 2011, which is hereby incorporated by reference.

BACKGROUND

The present disclosure generally relates to clinical analysis and medical diagnostics and, in particular, to an apparatus and process for opening/closing fluid containers for containing samples and/or one or more reagents.

In recent years, a strong demand for the automated analysis of liquid samples can be observed primarily due to an ongoing increase in the number of clinical analyses. Sample analysis typically involves combining samples with one or more reagents to determine the absence/presence and, optionally, the concentration of one or more analytes contained therein. Commercially available analyzers typically use pipetting robots for pipetting fluids. Since many reagents have to be cooled and/or prepared (e.g. mixed) before usage, it is convenient to leave the reagents in dedicated reagent containers for cool-storage and, as the case may be, preparation to thereupon withdraw portions thereof if needed. In order to avoid cross-contamination, spilling and evaporation, the reagent containers should be closed after usage.

It is known to use reagent containers comprising a container body with a container opening and a hinged cap pivotable with respect to the container body so as to open or close the container opening, e.g., by manual interaction, according to the specific demands of the user.

Therefore, there is a need to improve the automated process of analyzing samples involving the use of fluid containers with a hinged cap.

SUMMARY

According to the present disclosure, an apparatus for the automated opening/closing of one or more fluid containers for containing samples and/or one or more reagents is presented. Each fluid container has a body comprising an opening and a cap for closing the opening. The cap is pivotable with respect to the body so as to open or close the opening. The apparatus comprises a mount and a carriage supported by the mount by a translating mechanism that bidirectionally translates the carriage with respect to the mount. The carriage comprises a base portion and a pivoting portion supported by the base portion by a pivoting mechanism that bidirectionally pivots the pivoting portion with respect to the base portion. The pivoting portion has at least one contact member in contact with at least one projecting portion of the cap of each of the one or more fluid containers while pivoting the pivoting portion so as to open and optionally close the opening. The apparatus also comprises a drive coupled to the carriage for translating the base portion and pivoting the pivoting portion.

Accordingly, it is a feature of the embodiments of the present disclosure to to improve the automated process of analyzing samples involving the use of fluid containers with a hinged cap. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure. In this regard, terminology with respect to orientations and directions such as "horizontal", "vertical", "upper", "lower" is used with reference to the orientation of the figures being described. Because the components described can be positioned in a number of different orientations, this terminology is used for the purpose of illustration only and is in no way limiting.

As used herein, the term "opening/closing" generally relates to the opening and optionally closing of fluid containers. The term relates to the opening of fluid containers (with or without closing the fluid containers). It further relates to the opening and closing of fluid containers. The term "fluid containers" generally refers to containers for containing samples and/or one or more reagents, each of which comprises a body with an opening to be opened or closed by a cap, such as, but not limited to, a hinged cap pivotably fixed to the body and a separate cap that can be removed from the body. Examples for fluid containers are sample tubes with separate or hinged caps, sample cups with separate or hinged caps, single reagent containers and reagent cassettes comprising a plurality of reagent containers, e.g., serially arranged (stacked) with respect to each other.

According to one embodiment, an apparatus for the automated opening/closing of one or more fluid containers is proposed. Each cap can be pivotable with respect to the container body so as to be bi-directionally pivoted in an opening direction to open the container opening or in a closing direction to close the container opening. The apparatus can be useful for the simultaneous opening/closing of plural fluid containers which can, e.g., be in a fixed stacked arrangement such as a cassette.

The apparatus can also comprise a mount and a carriage movably supported by the mount by a translating mechanism so as to be bi-directionally moved (translated) with respect to the mount towards and away from the fluid containers. In other words, the carrier can be translatable with respect to the mount, e.g., between a first translating position farther away from the one or more fluid containers and a second translating position closer to the one or more fluid containers. As used herein, the terms "translation", "translated" or "translatable" refer to a linear (non-rotational) movement of the carriage relative to the mount.

The carriage can comprise a base portion and a pivoting portion pivotably supported by the base portion by a pivoting mechanism so as to be bidirectionally pivoted with respect to the base portion. The pivoting portion can have at least one contact member contacting at least one projecting portion of the cap of each of the one or more fluid containers in the course of pivoting the pivoting portion so as to pivot the cap to open and optionally close the container opening. By pivoting the pivoting portion in one pivoting direction (opening direction), the cap of each of the fluid containers can be pivoted to open the opening portion, and, by pivoting the pivoting portion in the other pivoting direction (closing direction), the cap of each of the fluid containers can be pivoted to close the opening portion. Hence, the pivoting portion can be pivotable with respect to the base portion, e.g., between a first pivoting position related to an closing position of the cap of each of the fluid containers in which the container opening is closed and a second pivoting position related to an opening position of the cap in which the container opening is opened. The pivoting portion can be, e.g., pivoted with respect to the base portion in the second translating position.

The apparatus can further comprise one drive, for example a linear drive such as, but not limited to a spindle drive, coupled to the carriage in a manner to translate the carriage and base portion, respectively, with respect to the mount towards and away from the one or more fluid containers and to pivot the pivoting portion with respect to the base portion.

Accordingly, the apparatus can advantageously enable one or a plurality of fluid containers to be simultaneously opened and optionally closed. Due to the fact that the carriage can be translated towards and away from the fluid containers to open/close the cap of each of the fluid containers by pivoting the pivoting portion thereof, the apparatus can advantageously be made small in vertical dimension thus leaving more free space above the fluid containers enabling unhindered access to the fluid containers, e.g., by a pipettor or any other instrument used for manipulating fluids contained in the fluid containers such as, but not limited to, a fluid mixer. In general, any device for manipulating the fluids contained in the fluid containers can advantageously be arranged above the fluid containers.

In the apparatus, the pivoting portion can be pivotably supported by the base portion by a pivoting mechanism so as to pivot the caps of the fluid containers to open and optionally close the container openings. According to one embodiment, the pivoting portion can be coupled to a pre-tensioning member, such as a spring, pre-tensioning the pivoting portion with respect to the base portion in one pivoting direction (closing direction) related to pivot the cap of each of the fluid containers to close the container opening.

In the above embodiment, the drive can advantageously be coupled to the pivoting portion for both translating the carriage towards and away from the one or more fluid containers and pivoting the pivoting portion wherein translation of the carriage can be separated (decoupled) from pivoting of the pivoting portion by the pre-tensioning member so as to have separate movements of the carriage and base portion, respectively, and the pivoting portion. The carriage can, for instance, be translated from the first translating position to the second translating position while keeping the pivoting portion in the first pivoting position, followed by pivoting the pivoting portion from the first pivoting position to the second pivoting position while keeping the base portion in the second translating position. Hence, opening of the one or more fluid containers can be facilitated by keeping the fluid containers stationary with respect to the apparatus by the base portion and by pivoting the caps by the pivoting portion. The pre-tensioning force of the pre-tensioning member can be used to firstly pivot the pivoting portion from the second pivoting position to the first pivoting position while keeping the base portion in the second translating position, followed by translating the carriage from the second translating position to the first translating position while keeping the pivoting portion in the first pivoting position. Hence, also closing of the one or more fluid containers can be facilitated by keeping the fluid containers stationary with respect to the apparatus by the base portion and by pivoting the caps by the pivoting portion, followed by removing the apparatus from the fluid containers.

In the apparatus, translation of the carriage towards the one or more fluid containers can, e.g. be stopped by a carriage-fixed stop member that abuts against a second stop member fixed with respect to the mount. When using one drive coupled to the pivoting member for both translating the carriage and pivoting the pivoting member, pre-tensioning of the pivoting portion towards the base portion can result in a separated translation of the carriage and pivoting of the pivoting portion so that the driving force is solely transferred to translation of the carriage until the carriage is stopped. Otherwise, stop of the carriage and base portion, respectively, by the stop members can result in a transfer of the driving force to a pivoting of the pivoting portion overriding the pre-tensioning force of the pre-tensioning member. Accordingly, abutment of the stop members can advantageously be used to pre-define a translating position (second translating position) to stop further translation and pivoting the pivoting portion.

According to another embodiment, the apparatus can comprise a controllable holding member to hold the base portion in a stationary position (second translating position) so as to pivot the pivoting portion relative to the base portion without further translation of the base portion. Also by this measure, separation (decoupling) of pivoting of the pivoting portion and translation of the carriage can advantageously be achieved so as to facilitate opening/closing of fluid containers. The holding member can advantageously be combined with the pre-tensioning member so as to obtain a combined effect in separating the translational and pivoting movements of the base and pivoting portions, respectively.

According to another embodiment, the at least one contact member for contacting the at least one projecting portion of the cap of each of one or more fluid containers can have one or more recesses, each of which can accommodate one projecting portion. Hence, the at least one contact member can advantageously be used to both pivot the caps in one direction to open the fluid containers and to pivot the caps in the reverse direction entraining the projection portions accommodated in the recesses.

According to a yet another embodiment, the apparatus can comprise at least one lower or first contact member to contact the at least one projecting portion of the cap of each of the one or more fluid containers in a manner to pivot the cap in one direction (opening direction) to open the container opening by pivoting the pivoting portion in opening direction, and at least one upper or second contact member to contact the at least one projecting portion of the cap of each of the one or more fluid containers in a manner to pivot the cap in the reverse direction by pivoting the pivoting portion in the other (reverse) direction (closing direction). Accordingly, the one or more fluid containers can advantageously both be opened by the at least one first contact member and can be closed by the at least one second contact member.

According to a yet another embodiment, the apparatus can open/close one or more fluid containers, each of which has a cap closing mechanism having a first cap closing position and a second cap closing position, wherein the first cap closing position can strongly affix the cap to the container body with respect to the second cap closing position. The pivoting portion can comprise at least one contact member to contact the at least one projecting portion of the cap of each of the one or more fluid containers in a manner to both rotate the cap in one direction to open the container opening by pivoting the pivoting portion in one pivoting direction (opening direction) and to pivot the cap in the reverse direction to place the cap in the second cap closing position by pivoting the pivoting portion in the other (reverse) pivoting direction (closing direction). Accordingly, the one or more fluid containers can advantageously both be opened by the at least one contact member and closed by positioning the cap in the second cap closing position. The at least one contact member can include one or more recesses, each of which can accommodate one projecting portion so that the fluid containers can be closed by pivoting the pivoting portion in closing direction thereby entraining the projection portions accommodated in the recesses so as to position the cap in the second cap closing position. In this embodiment, the pivoting portion can comprise at least one lower or first contact member to contact the at least one projecting portion of the cap of each one of the one or more fluid containers in manner to pivot the cap in one direction to open the container opening by pivoting the pivoting portion in the one pivoting direction (opening direction), and at least one upper or second contact member to contact the at least one projecting portion of the cap of each one of the one or more fluid containers in a manner to pivot the cap in the reverse direction so as to place the cap in the first cap closing position by pivoting the pivoting portion in the reverse pivoting direction (closing direction). Accordingly, the one or more fluid containers can advantageously both be opened by the at least one first contact member and closed by placing the cap in the first cap closing position by the at least one second contact member.

In the above embodiment, the at least one contact member can pivot the cap of each one of the one or more fluid containers being in the first cap closing position to open the container opening by translating the carriage towards the one or more fluid containers. Accordingly, an (initial) opening (e.g. breaking open) of the fluid containers can advantageously be reached by translating the carriage towards the one or more fluid containers.

According to a yet another embodiment, the pivoting portion can have one or more through-holes, each of which being arranged in a manner to provide access to the container opening of one fluid container. Accordingly, fluids contained in the fluid containers can advantageously be manipulated, e.g., by performing pipetting operations or by mixing the fluid, without removing the apparatus for opening/closing the fluid containers so as to save time in processing and/or analyzing samples.

According to a yet another embodiment, the base portion can comprise at least one down-holding member to contact the container body of each of the one or more fluid containers (e.g. in the second translating position of the base portion) while pivoting the cap to open or close the container opening. Hence, the fluid containers can be reliably opened and closed in easy manner. This can apply to the case of separating the translational and pivoting movements of the carriage and pivoting portion, respectively.

According to an embodiment, a new system for analyzing samples involving opening/closing of one or more fluid containers is proposed. The system can comprise an apparatus for the automated opening/closing of the one or more fluid containers as above-detailed, and at least one manipulator for manipulating fluids contained in the one or more fluid containers, such as, but not limited to, a pipettor having one or more pipettes for pipetting fluid contained in the one or more fluid containers, a mixer for mixing fluid contained in the one or more fluid containers, and the like. The system of the invention can, e.g., perform the automated analysis of samples by performing tests or assays related to various immunochemical and/or clinical-chemical analysis items.

According to another embodiment, a method for opening/closing one or more fluid containers is proposed. The method can comprise translating a carriage comprising a base portion and a rotating portion pivotably supported by the base portion towards the one or more fluid containers, pivoting the pivoting portion relative to the base portion thereby contacting at least one projecting portion of the cap of each one of the one or more fluid containers by at least one contact member of the pivoting portion so as to pivot the cap in one direction and optionally in the reverse direction to open and optionally close the container opening. Translating the carriage can comprise the base portion towards the one or more fluid containers. Pivoting the pivoting portion can comprise holding the base portion in a stationary position while pivoting the pivoting portion with respect to the base portion. Accordingly, as with the above apparatus, a separation of the translational and pivoting movements of the carriage and pivoting portion can advantageously be obtained to thereby facilitate the opening and closing of the one or more fluid containers.

According to a embodiment of the method, pivoting the pivoting portion to open the container opening of each of the one or more fluid containers can comprise contacting the at least one projecting portion by at least one first or lower contact member and pivoting the pivoting portion to close the container opening can comprise contacting the at least one projecting portion by at least one second or upper contact member. Hence, the container opening of the one or more fluid containers can readily be opened or closed according to the specific demands of the user.

According to another embodiment of the method, the method can open/close one or more fluid containers, each of which has a cap closing mechanism having a first cap closing position and a second cap closing position, wherein the first cap closing position can strongly affix the cap to the container body with respect to the second cap closing position. Pivoting the pivoting portion to pivot the cap of each of the one or more fluid containers to close the container opening can comprise placing the cap in the second cap closing position. Pivoting the pivoting portion to pivot the cap of each one of the one or more fluid containers to close the container opening may also comprise placing the cap in the first cap closing position thereby contacting the at least one projecting portion of the cap of each one of the one or more fluid containers by at least one second contact member. In above embodiment, the at least projecting portion of the cap of the one or more fluid containers is contacted by at least one member in a manner to initially open (break open) the fluid container by pivoting the cap of each one of the one or more fluid containers by translating the carriage towards the one or more fluid containers. The cap can, e.g., be positioned in the first cap closing position.

The method can also comprise pipetting fluid contained in the one or more fluid containers between the steps of opening and closing the fluid containers.

First, reference is made to FIG. 1 and FIGS. 2A-C illustrating an exemplary embodiment of the apparatus 1. The apparatus 1 can comprise a mount 2 used to fix the apparatus 1 to a base plate of an instrument for analyzing liquid samples which can be related to various clinical-chemical and/or immunochemical analysis items. The apparatus 1 can further comprise a carriage 3 movably supported by the mount 2 by a translating mechanism such as, for example, rollers 7 guided by linear guiding rails 8. Guided by the rails 8, the carriage 3 can be bidirectionally moved in a substantially horizontal plane with respect to the mount 2. Specifically, the carriage 3 can be reciprocally moved between two stop positions, i.e., a first translating position and a second translating position by translating the carriage 3 along first and second translating directions towards and away from a cassette 4.

Figure 1:
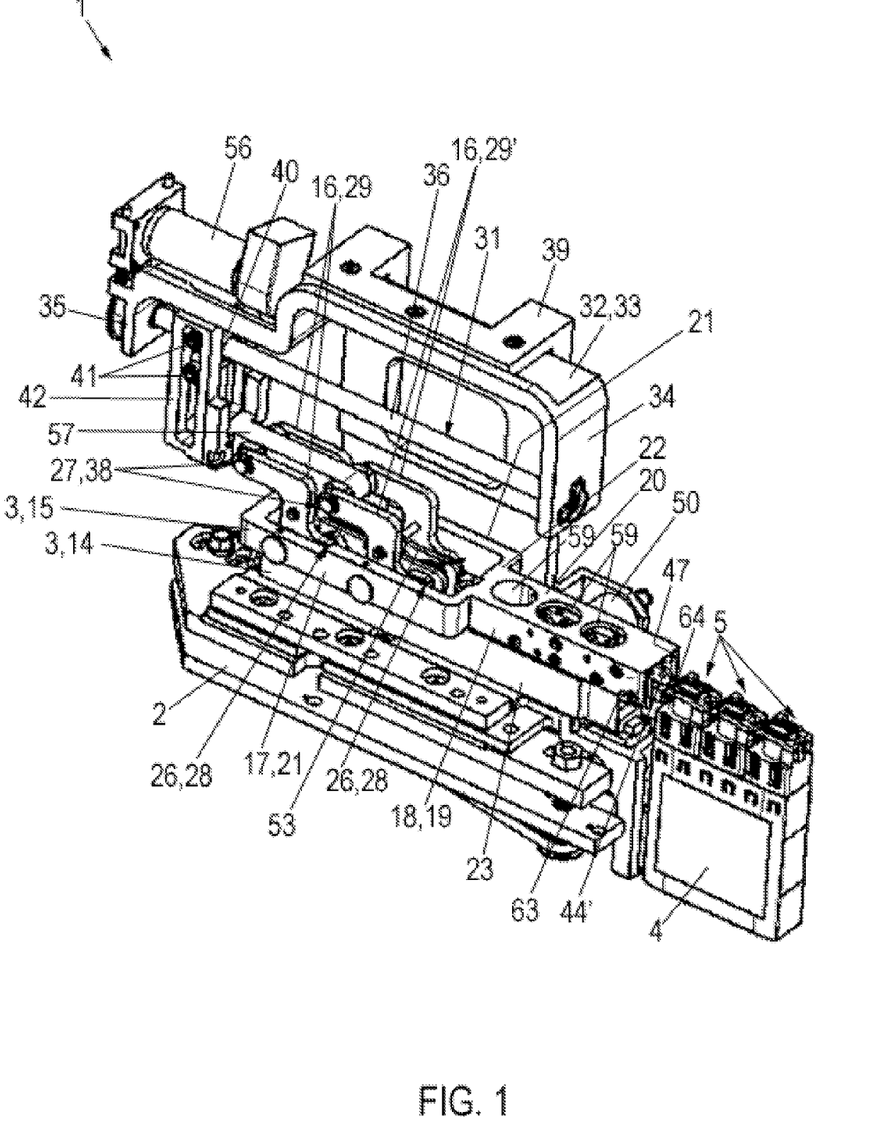
FIG. 1 illustrates a perspective view of the apparatus according to an embodiment of the present disclosure.
Figure 2A:
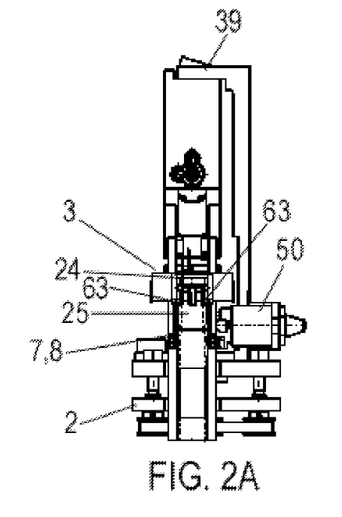
FIG. 2A illustrates is a front view of the apparatus of FIG. 1 according to an embodiment of the present disclosure.
Figure 2B:
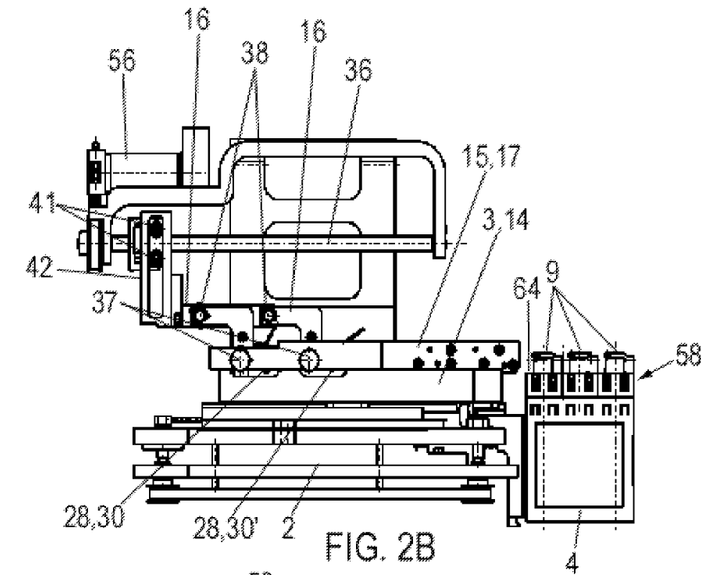
FIG. 2B illustrates is a side view of the apparatus of FIG. 1 according to an embodiment of the present disclosure.
Figure 2C:
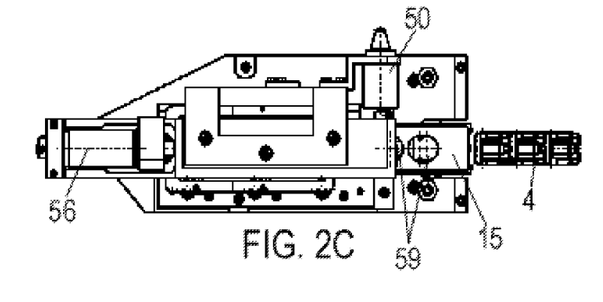
FIG. 2C illustrates is a top view of the apparatus of FIG. 1 according to an embodiment of the present disclosure.

The cassette 4 can comprise a number of fluid containers 5 that can be fixed in serial arrangement with respect to each other. In one exemplary embodiment, the cassette 4 can comprise three fluid containers 5. Each fluid container 5 can comprise a container body 6 for filling with fluid having an opening 10 closed by a cap 9 that is pivotably fixed (hinged) to the container body 6 so as to open the opening 10 by pivoting the cap 9 in the one pivoting direction (opening direction) and to close the opening 10 by pivoting the cap 9 in the other (reverse) pivoting direction (closing direction). Hence, each fluid container 5 can be repeatedly opened and closed according to the specific demands of the user.

In the illustrated embodiment, each fluid container 5 can comprise a cap closing mechanism 11 having a first cap closing position and a second cap closing position wherein in the first cap closing position ("hard close") the cap 9 can strongly be affixed to the container body 6 with respect to the second cap closing position ("soft close"). For instance, in the first cap closing position, the cap 9 can be locked by a locking mechanism whereas the cap 9 just plugs the opening 10 without securing the cap 9 to the container body 6 in the second cap closing position. Accordingly, while the first cap closing position can typically be used to transport or cool-store the cassette 4, the second cap closing position can mainly serve to prevent evaporation, spilling and contamination of fluids contained in the fluid containers 5 while in use. When using the fluid containers 5 for the first time, the caps 9 can typically be in the first cap closing position and, thus, have to be initially opened. Since each fluid container 5 can have a metallic leaf spring 12 pre-tensioning the cap 9 in closing direction, the cap 9 can be automatically pivoted in the second cap closing position to close the container opening 10.

Furthermore, as illustrated in FIG. 1, each cap 9 can have two projection portions 13 laterally projecting from the cap 9 in a substantially horizontal plane on two opposing sides of the cap 9 for rotating the cap 9 in opening and closing directions. In one exemplary embodiment, the two projection portions 13 can be cylindrical pins.

The carriage 3 can comprise a lower or base portion 14 and an upper or pivoting portion 15 pivotably supported by the base portion 14 and can be comprised of a front part 17 and a rear part 18. The front part 17, the outer contour, of which can be parallelepiped-shaped, can comprise two opposing vertical upper side walls 19 interconnected by a horizontal top wall 20 commonly surrounding an upper hollow space 24. The frame-like rear part 18 can comprise two longitudinal beams 21 and two cross beams 22 wherein the front part 17 can be fixed to the front cross beam 22. The base portion 14 can comprise two opposing vertical lower side walls 23 connected to the upper side walls 19 of the pivoting portion 15 commonly surrounding a lower hollow space 25.

The pivoting portion 15 can be pivotably supported by the base portion 14 by a pivoting mechanism such as, for example, two horizontally arranged pairs 29, 29' of opposing pivot arms 16, each of which having a substantially S-like shape. The pivoting mechanism can include a front pair 29 and a rear pear 29' wherein a lower end portion 26 of each of the pivot arms 16 can be rotatably linked to the lower side walls 23 of the base portion 14 by a lower pivot joint 28 so that the pivot arms 16 can be pivoted with respect to the base portion 14. The front pair 29 of pivot arms 16 can have a common pivoting axis 30 and the rear pair 29' of pivot arms 16 can have a common rear pivoting axis 30'.

The rear part 18 of the pivoting portion 15 can be rotatably linked to an intermediate portion of the pivot arms 16 by intermediate pivot joints 37 wherein the pivot arms 16 can extend through the frame-like rear part 18. Hence, pivoting the front and rear pair 29, 29' of pivot arms 16 around the front and rear pivoting axis 30, 30', respectively, the pivoting portion 15 can be pivoted with respect to the base portion 14.

The apparatus 1 can include a driven spindle drive 31 operatively coupled to the pivoting portion 15 for both translating the carriage 3 towards and away from the cassette 4 and pivoting the pivoting portion 15 with respect to the base portion 14. The spindle drive 31 can include a frame 32 comprised of an essentially horizontal upper plate 33 interconnecting two opposing vertical plates, i.e. a front plate 34 and a rear plate 35, which commonly rotatably support an essentially horizontally aligned spindle 36. The upper plate 33 can be affixed securely to a vertical rear panel 39 connected to the mount 2. Hence, by rotating the spindle 36, a spindle nut 40 can be reciprocally translated along the spindle 36 wherein a driven shaft of an electric motor 56 can be rotatably coupled to the spindle 36 so as to rotate the spindle 36 in both rotating directions.

In the spindle drive 31, the spindle nut 40 can be connected to two vertically arranged pairs of opposing guiding rolls 41 so as to be entrained by the spindle nut 40 translated along the spindle 36. Otherwise, the guiding rolls 41 can be accommodated in a vertical guiding cage 42 for guidance in vertical direction. The guiding cage 42 can be connected to the front and rear pairs 29, 29' of pivot arms 16. In one embodiment, the guiding cage 42 can be fixed to two superposed connecting plates 57 rotatably connected to upper end portions 27 of the pivot arms 16 by upper pivot joints 38.

Accordingly, by rotating the spindle 36, the spindle nut 40 can be translated along the spindle 36 entraining the guide rolls 41 accommodated within the guiding cage 42 so as to pivot the front and rear pair 29, 29' of pivot arms 16 wherein the guide rolls 41 can be vertically moved with respect to and guided by the guiding cage 42. Hence, driven by the spindle drive 31, the pivoting portion 15 can be bidirectionally pivoted with respect to the base portion 14 so as to reciprocally move the pivoting portion 15 between two stop positions, i.e., a first pivoting position and a second pivoting position along first and second pivoting directions.

The apparatus 1 can be used to open and optionally close the caps 9 of each of the fluid containers 5 of the cassette 4 positioned in front of the apparatus 1, i.e., in the translation path of the carriage 3. For pivoting the caps 9 in opening direction and optionally closing direction, the front part 17 of the pivoting portion 15 can have at least one pair 43, 43' of contact rods 44, 44', 45, 45' fixed to inner faces 47 of the upper side walls 19 for contacting the projection portions 13 of the caps 9 in the second translating position of the carriage 3.

Figure 3A:
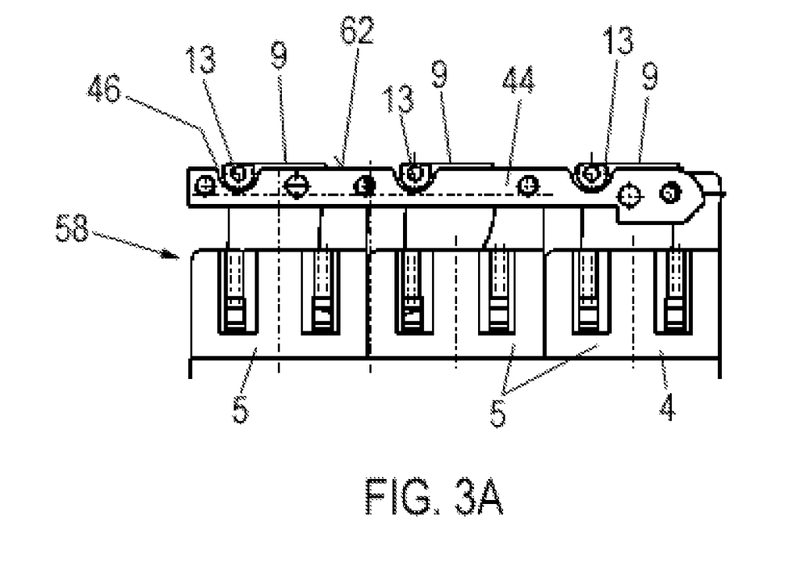
FIGS. 3A-B illustrate perspective views of an enlarged detail of the pivoting portion of the apparatus of FIG. 1 according to an embodiment of the present disclosure.
Figure 3B:
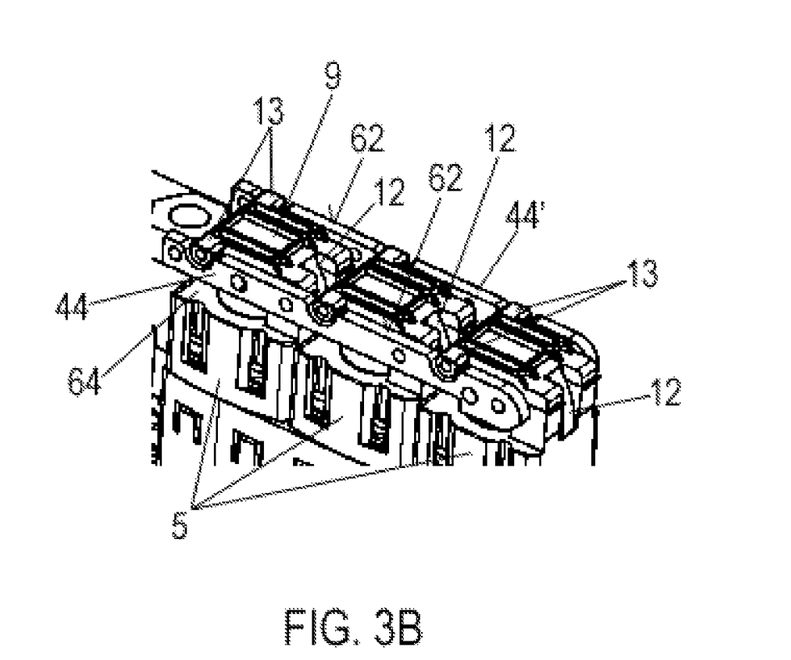

As illustrated in FIGS. 3A-B, in one embodiment, the front part 17 of the pivoting portion 15 can have one pair 43 of two opposing lower contact rods 44, 44' that can be securely fixed to the two opposing vertical inner faces 47 of the upper side walls 19. The lower contact rods 44, 44' can be arranged in a manner to contact the projecting portions 13 or to be brought in contact with the projecting portions 13 by pivoting the pivoting portion 15 when the carriage 3 is in the second translating position with respect to the mount 2. As shown, each of the lower contact rods 44, 44' can have an upper guiding face 62 comprising a number of semi-circular recesses 46 serially arranged with respect to each other for inserting the projecting portions 13 of the caps 9. In an exemplary embodiment, the upper guiding face 62 can comprise three semi-circular recesses 46. Hence, the lower contact rods 44, 44' can be used to pivot the caps 9 in opening direction to open the fluid containers 5, and, due to inserting the projecting portions 13 in the recesses 46, can also be used to pivot the caps 9 in closing direction. Otherwise, the base portion 14 can hold the fluid containers 5 down while pivoting the caps 9 in opening or closing directions to open or close the openings 10. The base portion 14 can have two opposing interior struts 63 which, in the second translational position of the carriage 3 can be placed in contact with upper shoulders 64 of the fluid containers 5. As a result, the fluid containers 5 can be held down in a stationary position while pivoting the caps 9 to open or close the container openings 10 by pivoting the pivoting portion 15.

Figure 4A:
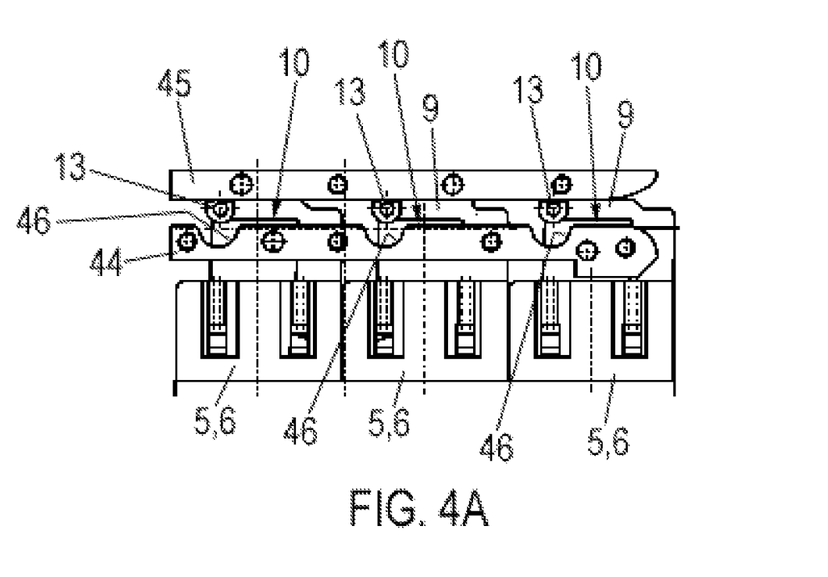
FIGS. 4A-B illustrate perspective views of a variant of the pivoting portion of the apparatus of FIG. 1 according to an embodiment of the present disclosure.
Figure 4B:
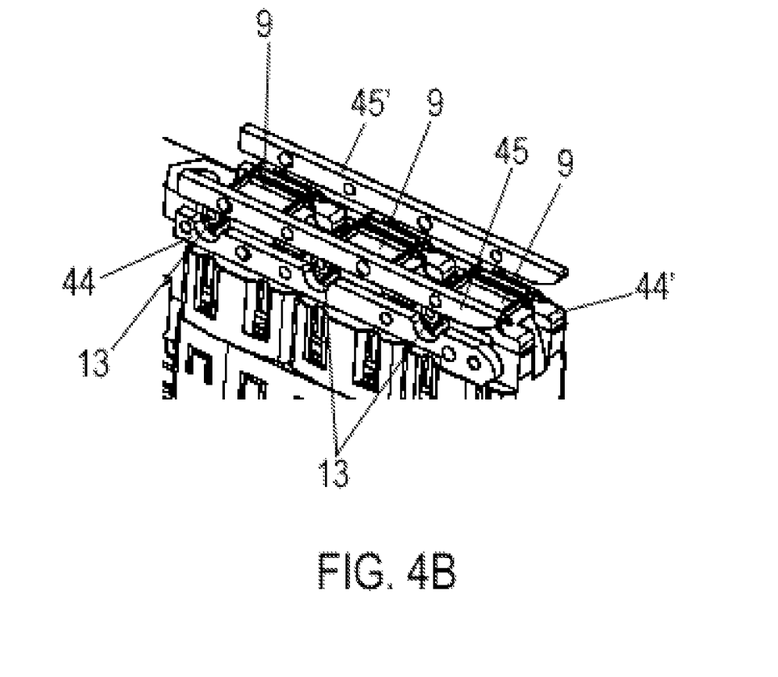

As illustrated in FIGS. 4A-B, in another embodiment, the front part 17 of the pivoting portion 15 can have one pair 43 of two opposing lower contact rods 44, 44' and one pair 43' of two opposing upper contact rods 45, 45' that can be securely fixed to the two opposing vertical inner faces 47 of the upper side walls 19. The two pairs 43, 43' of contact rods 44, 44', 45, 45' can be stacked one upon the other in vertical direction so that the projecting portions 15 of the caps 9 can be positioned in-between the upper and lower contact rods 44, 44', 45, 45'. The lower contact rods 44, 44' can be used to pivot the caps 9 in opening direction to open the fluid containers 5. The upper contact rods 45, 45' can be used to pivot the caps 9 in the reverse or closing direction to close the fluid containers 5. Both the lower contact rods 44, 44' and the upper contact rods 45, 45' can be arranged in a manner to contact the projecting portions 13 or to be brought in contact with the projecting portions 13 by pivoting the pivoting portion 15 when the carriage 3 is in the second translational position with respect to the mount 2, wherein the projecting portions 13 can be arranged in-between the upper and lower contact rods 45, 45', 44, 44'.

Figure 5:
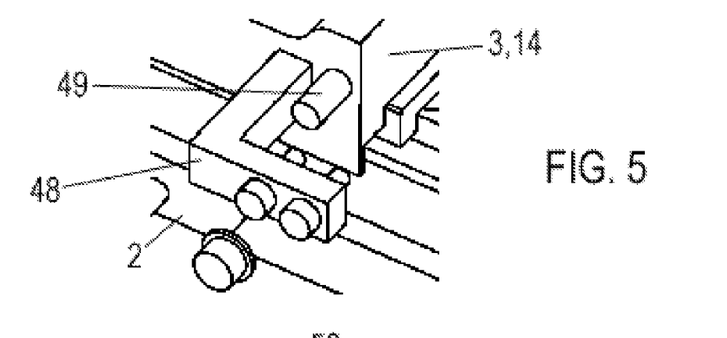
FIG. 5 illustrates a perspective view of an exemplary embodiment of the stop members of the apparatus of FIG. 1 according to an embodiment of the present disclosure.

With reference to FIG. 5, the apparatus 1 can further include a first stop member 48 fixed to the mount 2 and a second stop member 49 fixed to the carriage 3, the stop members 48, 49 can be arranged to stop translational movement of the carriage 3 towards the cassette 4 in the second translational position.

Figure 6:
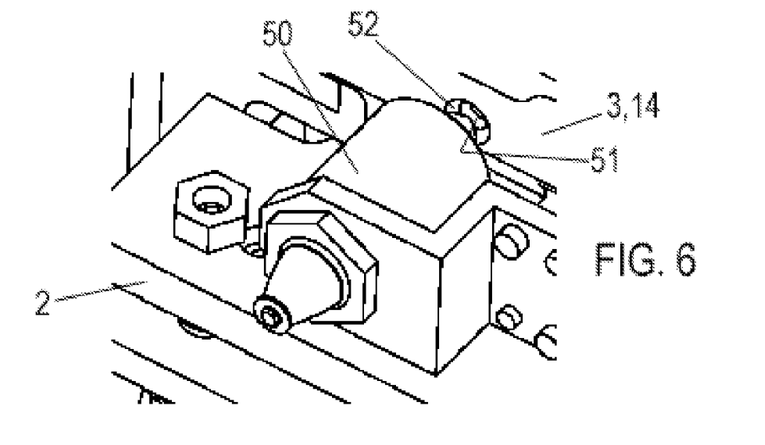
FIG. 6 illustrates a perspective view of an electromagnet for holding the carriage of the apparatus of FIG. 1 in a stationary translational position according to an embodiment of the present disclosure.

With reference to FIG. 6, the apparatus 1 can further include a controllable holding member for actively holding the carriage 3 and base portion 14, respectively, in the second translational position. As illustrated, the holding member can be, for example, an electro-magnet 50 which can be supplied with current so as to magnetically attract a metallic counter piece 51 arranged within a depression 52 on the outer side of the base portion 14 of the carriage 3.

Figure 7:
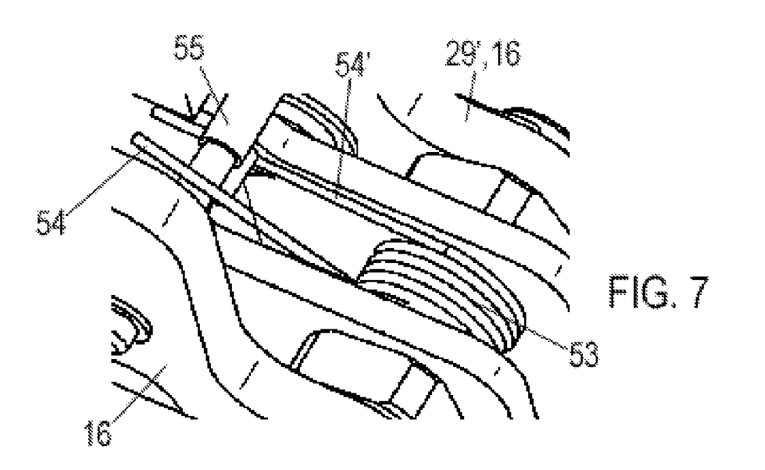
FIG. 7 illustrates a perspective view of a spring for pre-tensioning the pivoting portion of the apparatus of FIG. 1 towards the base portion according to an embodiment of the present disclosure.

With reference to FIG. 7, the apparatus 1 can further include a pre-tensioning member for pre-tensioning the pivoting portion 15 with respect to the base portion 14. As illustrated, the pre-tensioning member can be, for example, a coil spring 53 having two spring legs 54, the one spring leg 54 resting against the base portion 14 and the other spring leg 54' resting against a connecting link 55 connecting the front pair 29 of pivot arms 16. Hence, the pivoting portion 15 can be pre-tensioned for pivoting the caps 9 in closing direction.

Figure 8A:
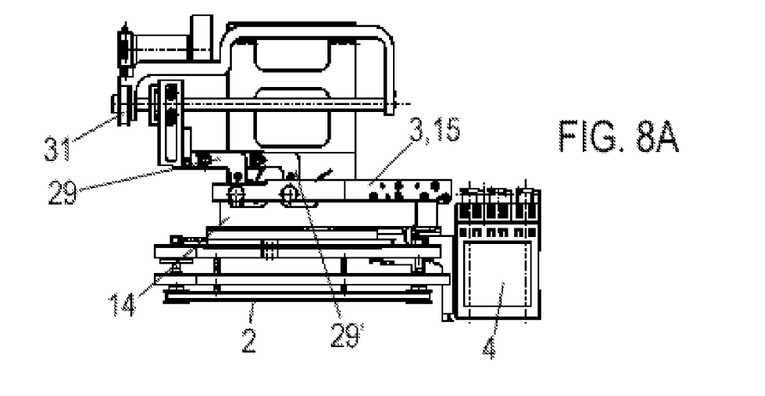
FIGS. 8A-F illustrate perspective views of the apparatus of FIG. 1 illustrating the process of opening the fluid containers of one cassette according to an embodiment of the present disclosure.
Figure 8B:
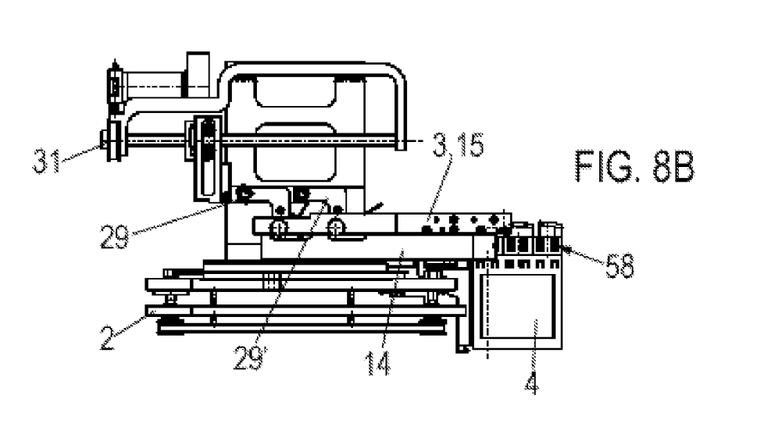
Figure 8C:
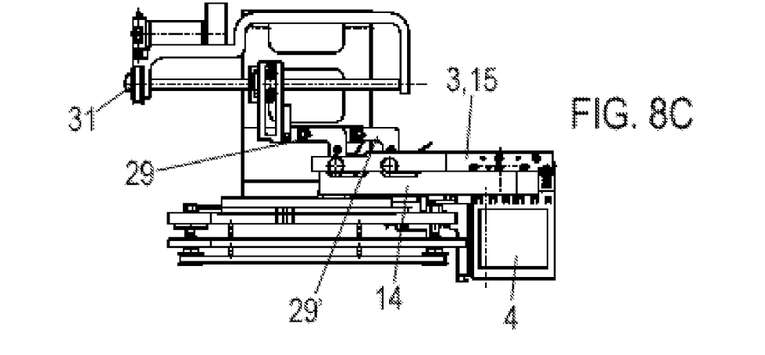

With reference to FIGS. 8A-F, in the following, an exemplary method of opening and closing the caps 9 of the fluid containers 5 of the cassette 4 by the apparatus 1 is described. The method can start as depicted in FIG. 8A, in which the carriage 3 can be in the first translational position with respect to the mount 2 wherein the pivoting portion 15 is non-rotated with respect to the base portion 14. Now, turning the spindle 36 in one direction by the electric motor 56, the spindle nut 40 can be moved towards the cassette 4 (in the figures to the right) thereby pushing the carriage 3 towards the cassette 4. By moving the carriage 3 towards the cassette 4, the upper and lower hollow spaces 24, 25 can be inserted in a top portion 58 of the cassette 4 (FIG. 8B) until the carriage 3 is stopped in the second translational position by the second stop member 49 abutting against the first stop member 48 (FIG. 8C).

While translating the carriage 3 from the first translational position to the second translational position, the pivoting portion 15 can be inhibited to pivot with respect to the base portion 14 due to the coil spring 53 pre-tensioning the pivoting portion 15 towards the base portion 14. To that effect, the spring force of the coil spring 53 can be chosen to be strong enough to inhibit pivoting even though the carriage 3 is pushed towards the cassette 4 by coupling the spindle nut 40 to the pivoting portion 15. Hence, translation of the carriage 3 can be timely separated (decoupled) from the pivoting of the pivoting portion 15. In the second translational position, the lower contact rods 44, 44' can be in a position where the projection portions 13 of the caps 9 can be right above the recesses 46 so as to be inserted in the recesses 46 by pivoting the pivoting portion 15. Otherwise, the two interior struts 63 of the base portion 14 can be in contact with the shoulders 64 of the fluid containers 5 so that the fluid containers 5 can be kept down by the base portion 14 in the second translational position of the carriage 3.

As illustrated in FIGS. 3A-B, depending on the specific embodiment of the lower contact rods 44, 44', in the second translational position of the carriage 3, the projection portions 13 of the caps 9 can be inserted (accommodated) in the recesses 46 prior to rotating the pivoting portion 15. As a result, the caps 9 can be slightly opened (initial opening) by translating the carriage 3 to the second translational position. Alternatively, in the second translational position of the carriage 3, the projection portions 13 can also be arranged right above the recesses 46 prior to pivoting the pivoting portion 15 without initial opening of the caps 9 by translating the carriage 3 to the second translational position.

In the embodiment depicted in FIGS. 4A-B, in the second translational position, the projection portions 13 can be in a position in-between the lower contact rods 44, 44' and the upper contact rods 45, 45' so as to be inserted in the recesses 46 by pivoting the pivoting portion 15. Alternatively, in the second translational position of the carriage 3, the projection portions 13 can also be accommodated in the recesses 46 so as initially open the caps 9 by translating the carriage 3 to the second translational position.

Figure 8D:
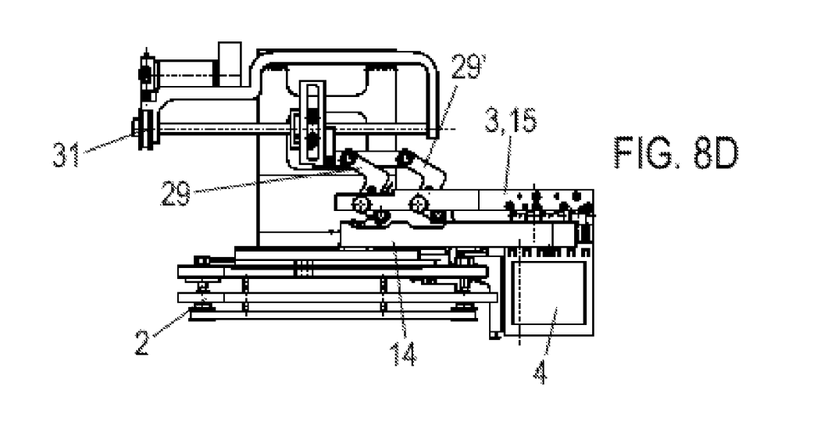
Figure 8E:
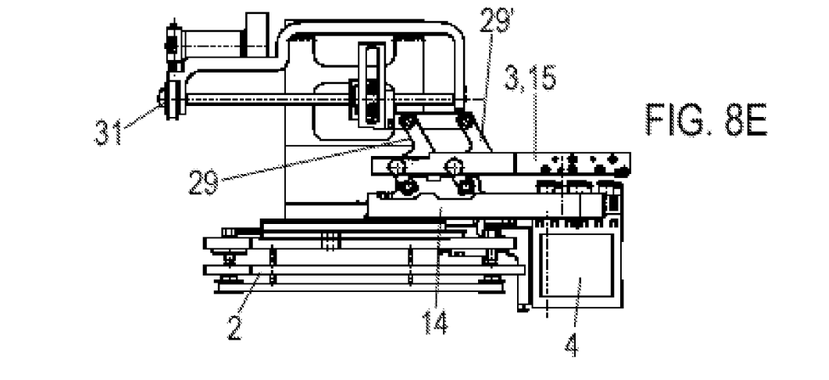
Figure 8F:
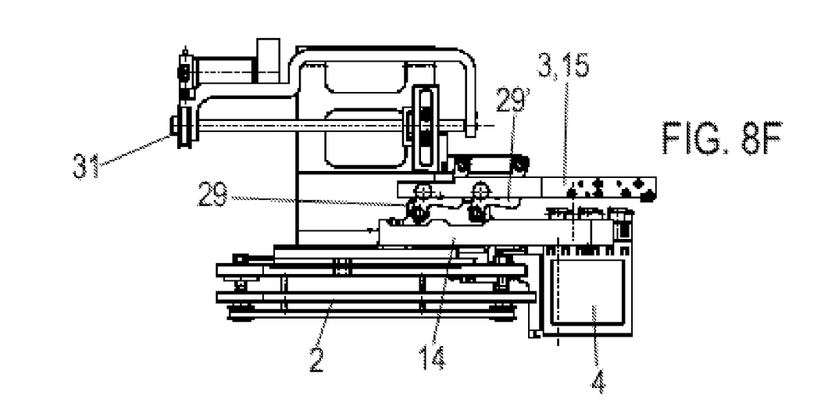

With reference to FIGS. 8D-F, starting from the second translational position of the carriage 3 where any further forward movement of the carriage 3 is blocked and the pivoting portion 15 is in the first pivoting position, a further linear movement of the spindle nut 40 towards the cassette 4 can cause the pivoting portion 15 to pivot with respect to the base portion 14 overcoming the spring force of the coil spring 53. As a result, the caps 9 of the fluid containers 5 can be pivoted in opening direction to open the openings 10 by pivoting the pivoting portion 15 from the first pivoting position to the second pivoting position, the latter one being defined by stopping rotation of the spindle 36. As illustrated, the contact rods 44, 44', 45, 45' can be kept substantially horizontal while pivoting the pivoting portion 15 relative to the base portion 14.

As, e.g., illustrated in FIG. 1, the top wall 20 of the front part 17 of the pivoting portion 15 can have a number of through-holes 59 arranged right above the openings 10 of the fluid containers 5 in the second pivoting position of the pivoting portion 15 so that fluids contained therein can be accessed from above, e.g., for mixing the fluids and/or performing pipetting operations. In an exemplary embodiment, the pivoting portion 15 can have three through-holes 59.

Starting with FIG. 8F, the fluid containers 5 can also be closed by pivoting the caps 9 in closing direction. By turning the spindle 36 in the reverse direction, the spindle nut 40 can be moved away from the cassette 4 (in the figures to the left) thereby pivoting the pivoting portion 15 in the reverse direction from the second pivoting position to the first pivoting position with respect to the base portion 14 while keeping the carriage 3 stationary in the second translational position. For this purpose, electric current can be supplied to the electromagnet 50 so as to magnetically attract the metallic counter piece 51 of the carriage 3 as shown in FIG. 6 to hold the base portion 14 in the second translational position. The spring force of the coil spring 53 can favor (assists) the reverse pivoting of the pivoting portion 15 so that the pivoting movement of the pivoting portion 15 relative to the base portion 14 can be paramount to the translating movement of the carriage 3 relative to the mount 2.

While pivoting the pivoting portion 15 in the reverse direction, the projecting portions 13 can be entrained by the semicircular recesses 46 of the lower contact rods 44, 44' to pivot the caps 9 in the closing direction. Supported by the elastic forces of the leaf springs 12, each cap 9 can be brought in the second cap closing position. In case of providing for the upper contact rods 45, 45', the caps 9 can be pushed in the second and optionally first cap closing position by the upper contact rods 45, 45' (FIGS. 8E-D).

With reference to FIGS. 8A-8C, starting from the second translational position of the carriage 3, the pivoting portion 15 being in the first pivoting position, further linear movement of the spindle nut 40 in the reverse direction can cause the carriage 3 to be translated with respect to the mount 3 (in the figures to the left side). As a result, the top portion 58 of the cassette 4 continuously leave the upper and lower hollow spaces 24, 25 until the carriage 3 is stopped in the first translational position by stopping rotation of the spindle 36.

Figure 9:
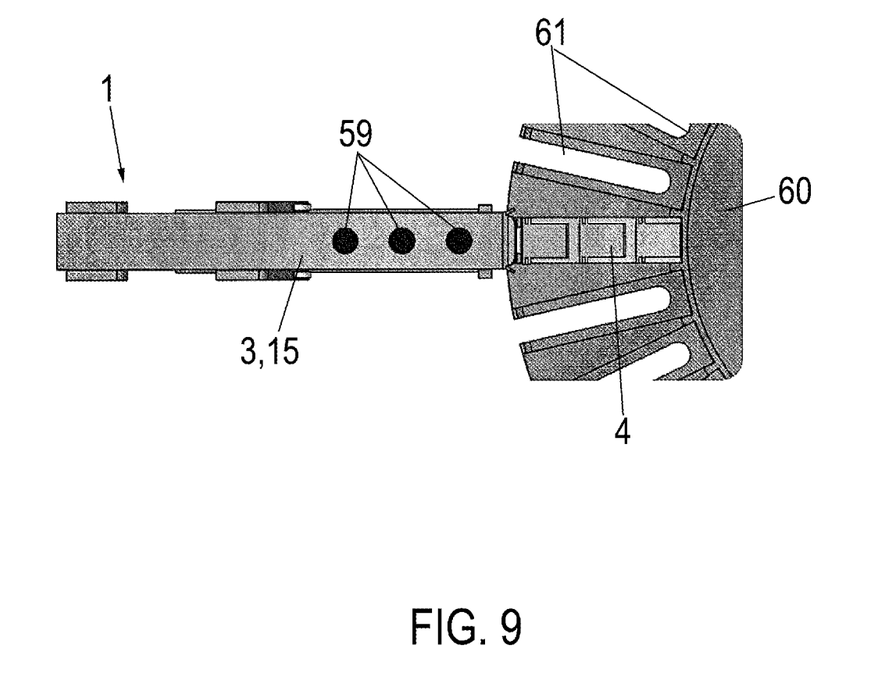
FIG. 9 illustrates a perspective view of the apparatus of FIG. 1 used for opening/closing a cassette placed on a rotor according to an embodiment of the present disclosure.

With reference to FIG. 9, an application of the apparatus 1 is described. The apparatus 1 can be operatively coupled to a rotatably driven rotor 60 having a plurality of seats 61, each of which holding one cassette 4. Driving the rotor 60, one of the cassettes 4 can be brought in a position right in front of the apparatus 1 so as to open the fluid containers 5 thereof, e.g., for performing pipetting operations of fluids contained therein. As illustrated, the apparatus 1 can be placed on the side of the rotor 60 which can advantageously result in a comparably small height. Otherwise, a pipettor for pipetting fluids or any other device for manipulating fluids contained in the cassettes 4 such as a mixer can be arranged above the cassettes 4 and/or the rotor 60 so that fluids contained in the fluid containers 5 can readily be accessed from above.

From the above description of the various exemplary embodiments, fluid containers can readily be opened and optionally closed by using the apparatus which can be made small in height and compact in shape so that the apparatus can easily be integrated in instruments for analyzing samples. Using only one drive for translating the carriage and pivoting the pivoting portion, e.g., coupled to the pivoting portion, the apparatus can be fabricated at comparably low cost. The apparatus can allow for the simultaneous opening of a plurality of, e.g., three fluid containers to thereby save time and costs for the processing of samples.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. An apparatus for the automated opening/closing of one or more fluid containers for containing samples and/or one or more reagents, each of which having a body comprising an opening and a cap for closing the opening, wherein the cap is pivotable with respect to the body so as to open or close the opening, the apparatus comprising:

a mount;

a carriage supported by the mount by a translating mechanism that bidirectionally translates the carriage with respect to the mount between a first translating position and a second translation portion, wherein the carriage comprising a base portion and a pivoting portion supported by the base portion by a pivoting mechanism that bidirectionally pivots the pivoting portion with respect to the base portion between a first pivoting position related to a closing position of the cap of each of the fluid containers in which the container opening is closed and a second pivoting position related to an opening position of the cap in which the container opening is opened, with the pivoting portion being pivoted with respect to the base portion in the second translating position, wherein the pivoting portion has at least one contact member in contact with at least one projecting portion of the cap of each of the one or more fluid containers while pivoting the pivoting portion so as to open and optionally close the opening and wherein the pivoting portion is coupled to a pre-tensioning member that pre-tensions the pivoting portion with respect to the base portion in a pivoting direction related to closing the opening of each of the one or more fluid containers; and one drive coupled to the carriage for translating the base portion and pivoting the pivoting portion.

2. The apparatus according to claim 1, wherein the carriage comprises a first stop member that abuts against a second stop member fixed with respect to the mount so as to stop translation of the carriage towards the one or more fluid containers.

3. The apparatus according to claim 1, wherein the drive is a linear drive coupled to the pivoting portion.

4. The apparatus according to claims 1, further comprising, a controllable holding member to hold the base portion in a stationary translating position while pivoting the pivoting portion with respect to the base portion.

5. The apparatus according to claim 1, wherein the at least one contact member has one or more recesses, each of which accommodates the projecting portion of the cap of one of the fluid containers so as to pivot the cap to open and optionally close the opening.

6. The apparatus according to claim 1, further comprising,
at least one first contact member to contact the at least one projecting portion of the cap of each of the one or more fluid containers so as to pivot the cap to open the opening; and
at least one second contact member to contact the at least one projecting portion of the cap of each of the one or more fluid containers so as to pivot the cap to close the opening.

7. The apparatus according to claim 1, wherein the pivoting portion has one or more through-holes, each of which being arranged in a manner to provide access to the opening of each one of the one or more fluid containers.

8. The apparatus according to claim 1, wherein the base portion comprises at least one down-holding member to contact the body of each one of the one or more fluid containers while pivoting the cap to open or close the opening.

9. A system for analyzing samples involving opening/closing of one or more fluid containers for containing samples and/or one or more reagents, each of which having a body comprising an opening and a cap for closing the opening, wherein the cap is pivotable with respect to the body so as to open or close the opening, the system comprising:
an apparatus for the automated opening/closing of the one or more fluid containers comprising,
a mount,
a carriage supported by the mount by a translating mechanism that bidirectionally translates the carriage with respect to the mount between a first translating position and a second translation portion, wherein the carriage comprising a base portion and a pivoting portion supported by the base portion by a pivoting mechanism that bidirectionally pivots the pivoting portion with respect to the base portion between a first pivoting position related to a closing position of the cap of each of the fluid containers in which the container opening is closed and a second pivoting position related to an opening position of the cap in which the container opening is opened, with the pivoting portion being pivoted with respect to the base portion in the second translating position, wherein the pivoting portion has at least one contact member to contact at least one projecting portion of the cap of each of the one or more fluid containers so as to open and optionally close the opening and wherein the pivoting portion is coupled to a pre-tensioning member that pre-tensions the pivoting portion with respect to the base portion in a pivoting direction related to closing the opening of each of the one or more fluid containers, and
one drive coupled to carriage for translation of the base portion and pivoting of the pivoting portion; and
at least one manipulator for manipulating fluids contained in the one or more fluid containers while having their caps opened.

10. A method for the automated opening/closing of one or more fluid containers for containing samples and/or one or more reagents, each of which having a body comprising an opening and a cap for closing the opening, wherein the cap is pivotable with respect to the body so as to open or close the opening, the method comprising:
translating a carriage comprising a base portion and a pivoting portion supported by the base portion towards the one or more fluid containers, wherein translating the carriage comprises translating the base portion towards the one or more fluid containers; and
pivoting the pivoting portion relative to the base portion thereby contacting at least one projecting portion of the cap of each one of the one or more fluid containers by at least one contact member of the pivoting portion so as to pivot the cap to open and optionally close the opening, wherein pivoting the pivoting portion comprises holding the base portion in a stationary position while pivoting the pivoting portion with respect to the base portion and wherein pivoting the pivoting portion to pivot the cap of each one of the one or more fluid containers to close the opening comprises placing the cap in the first cap closing position thereby contacting the at least one projecting portion of the cap of each one of the one or more fluid containers by at least one second contact member.

11. The method according to claim 10, wherein pivoting the pivoting portion to open the opening of each one of the one or more fluid containers comprises contacting the at least one projecting portion by at least one first contact member and wherein pivoting the pivoting portion to close the opening of each one of the one or more fluid containers comprises contacting the at least one projecting portion by at least one second contact member.

12. The method according to claim 10, wherein pivoting the pivoting portion to pivot the cap of each one of the one or more fluid containers to close the opening comprises placing the cap in a second cap closing position to fix the cap to the body in a less strong manner with respect to a first cap closing position.

13. The method according to claims 10, further comprising,
pipetting fluid contained in the one or more fluid containers between the opening and closing the fluid containers.

* * * * *